(12) United States Patent
Franco et al.

(10) Patent No.: US 11,871,750 B2
(45) Date of Patent: Jan. 16, 2024

(54) ANTIMICROBIAL BIOCOMPATIBLE CO-DOPED MAGNESIUM OXIDE NANOCOMPOSITE COMPOSITIONS

(71) Applicant: NSC—NANO SONO COOPERATION LTD, Yokneam Illit (IL)

(72) Inventors: Ariel Antonio Franco, Yokneam Illit (IL); Rajashekharayya A. Sanguramath, Yokneam Illit (IL); Asaf Hassin, Yokneam Illit (IL)

(73) Assignee: NSC—NANO SONO COOPERATION LTD, Yokneam Illit (IL)

( * ) Notice: Subject to any disclaimer, the term of this patent is extended or adjusted under 35 U.S.C. 154(b) by 0 days.

(21) Appl. No.: 17/688,915

(22) Filed: Mar. 8, 2022

(65) Prior Publication Data
US 2022/0279794 A1 Sep. 8, 2022

Related U.S. Application Data

(60) Provisional application No. 63/157,889, filed on Mar. 8, 2021.

(51) Int. Cl.

| | |
|---|---|
| *A01N 59/16* | (2006.01) |
| *A01N 25/08* | (2006.01) |
| *A01N 59/06* | (2006.01) |
| *A01N 59/00* | (2006.01) |
| *A61K 9/00* | (2006.01) |
| *A61K 33/30* | (2006.01) |
| *A61K 33/24* | (2019.01) |
| *A61K 33/06* | (2006.01) |
| *A61K 33/00* | (2006.01) |
| *A61K 47/02* | (2006.01) |
| *A01P 1/00* | (2006.01) |
| *A61P 31/02* | (2006.01) |
| *C09D 5/14* | (2006.01) |
| *A61L 15/44* | (2006.01) |
| *A61L 15/18* | (2006.01) |

(52) U.S. Cl.
CPC ............ *A01N 59/16* (2013.01); *A01N 25/08* (2013.01); *A01N 59/00* (2013.01); *A01N 59/06* (2013.01); *A01P 1/00* (2021.08); *A61K 9/0014* (2013.01); *A61K 33/00* (2013.01); *A61K 33/06* (2013.01); *A61K 33/24* (2013.01); *A61K 33/30* (2013.01); *A61K 47/02* (2013.01); *A61L 15/18* (2013.01); *A61L 15/44* (2013.01); *A61P 31/02* (2018.01); *C09D 5/14* (2013.01); *A61L 2300/102* (2013.01); *A61L 2300/404* (2013.01)

(58) Field of Classification Search
CPC ....................................................... A01N 59/16
See application file for complete search history.

(56) References Cited

U.S. PATENT DOCUMENTS

| | | | |
|---|---|---|---|
| 2015/0210558 A1* | 7/2015 | Dickinson | C01F 5/30 423/600 |
| 2016/0120184 A1* | 5/2016 | Gedanken | B82Y 30/00 424/641 |
| 2020/0023145 A1 | 7/2020 | Franco et al. | |

FOREIGN PATENT DOCUMENTS

| | | |
|---|---|---|
| CN | 103172092 | 6/2013 |
| CN | 108823795 | 11/2018 |
| CN | 111019426 | 4/2020 |
| WO | 2014181329 | 11/2014 |

OTHER PUBLICATIONS

Rajendran V. et al. Synthesis and Characterization of Li+, Ag2+and Cu2+ metals doped MgO nanostructured in Gel Method. IOP Conference Series: Materials Science and Engineering, vol. 360, Second International Conference on Materials Science and Technology (ICMST 2016), Jun. 5-8, 2016.

Rao Y. et al. Influence of different ions doping on the antibacterial properties of MgO nanopowders. Applied Surface Science, vol. 284, 2013, pp. 726-731 (Abstract only).

Zhang D. et al. Study of the microstructure and antibacterial properties of MgO with doped defects. Journal of Theoretical and Computational Chemistry, vol. 17, Issue 2, 2018, Article 1850018, pp. 1-13, ISSN (online) 1793-6888, <https://doi.org/10.1142/S0219633618500189>. (Mar. 29, 2018) (Abstract only).

Thakur N. et al. Effect of (Ag, Co) co-doping on the structural and antibacterial efficiency of CuO nanoparticles: A rapid microwave assisted method. Journal of Environmental Chemical Engineering, vol. 8, Issue 4, 2020, Article 104011, pp. 1-9, ISSN 2213-3437, <https://doi.org/10.1016/j.jece.2020.104011>. (May 8, 2020) (Abstract only).

Stankic et al., Pure and multi metal oxide nanoparticles: synthesis, antibacterial and cytotoxic properties, J. Nanobiotech, 14:73 (2016).

Amina et al., Biogenic green synthesis of MgO nanoparticles using Saussurea costus biomasses for a comprehensive detection of their antimicrobial, cytotoxicity against MCF-7 breast cancer cells and photocatalysis potentials, PLOS ONE, Aug. 14, 2020.

Jayapriya et al., One-step biological synthesis of cauliflower-like Ag/MgO nanocomposite with antibacterial, anticancer, and catalytic activity towards anthropogenic pollutants, Res. on Chem. Int., Jan. 4, 2020 (Abstract only).

Behzadi et al., Albumin binding and anticancer effect of magnesium oxide nanoparticles, Int. J. Nanomed., 2019, 14:257-270.

* cited by examiner

*Primary Examiner* — Sarah Alawadi
(74) *Attorney, Agent, or Firm* — JMB Davis Ben-David

(57) ABSTRACT

Described herein are co-doped magnesium oxide nanocomposites with antimicrobial properties for industrial and biomedical applications. Methods of inhibiting microbial and/or eliminating microbial growth with the disclosed compounds on biological and inanimate surfaces are also described.

18 Claims, 3 Drawing Sheets

ANTIMICROBIAL BIOCOMPATIBLE CO-DOPED MAGNESIUM OXIDE NANOCOMPOSITE COMPOSITIONS

CROSS REFERENCE TO RELATED APPLICATIONS

Benefit is claimed to U.S. Provisional Patent Application No. 63/157,889, filed on Mar. 8, 2021, the contents of which are incorporated by reference herein in their entirety.

FIELD

The present disclosure relates to co-doped magnesium oxide nanocomposites with antimicrobial properties and increased biocompatibility for industrial and biomedical applications. Methods of inhibiting microbial growth and/or eliminating microbial contamination with the disclosed compounds are also described.

BACKGROUND

Nanomaterials of magnesium oxide (nano MgO) show promising potential for biomedical applications. As a low cost and environmentally friendly material, these materials have already been widely applied in the process of neutralizing acid water and dye from wastewater. Over the past decade, the global consumption of MgO in wastewater treatment has utilized more than 48,000 tons annually. However, little attention has been paid to the cytotoxic and antibacterial activity of nano MgO.

Recently, studies of the interaction of an electrolytic nano MgO suspension on *E. coli* revealed that the nano MgO possesses antibacterial effects. These studies join previous work which described the antibacterial properties of several pure and doped metal oxide particles (Stankic et al., J. Nanobiotech, 14:73 (2016); and US Patent Pub. No. 2020/0231459). In addition to the antimicrobial effects, magnesium oxide compositions have also been observed to possess antineoplastic properties (Amina et al., PLOS ONE, Aug. 14, 2020; Jayapriya et al., Res. on Chem. Int., Jan. 4, 2020; and Behzadi et al., Int. J. Nanomed., 2019, 14:257-270). However, despite these promising antibacterial and antineoplastic properties, significant questions remain regarding toxicity (both environmental and biological) and biocompatibility of metal oxide nanomaterials (Sengui and Asmatulu, Env. Chem. Letters 18, pp. 1659-1683 (2020).

Thus, a continuing need exists for development of metal oxide nanomaterials that possess strong antimicrobial and antineoplastic properties, yet are also sufficiently biocompatible and non-toxic for human and animal use.

SUMMARY

Provided herein are novel antimicrobial metal oxide nanomaterials that are additionally biocompatible so as to be suitable for human and animal use. The nanomaterials described herein are co-doped magnesium oxide nanocomposite compositions that include a magnesium oxide doped with metal A and B, in which metal A is a transition metal selected from titanium, vanadium, manganese, iron, zirconium, niobium, silver, and zinc; and metal B is an alkali or alkaline earth metal selected from lithium, sodium, potassium, calcium, strontium, and barium, and wherein the co-doped magnesium oxide nanocomposite possesses a crystalline periclase structure.

In particular embodiments of the co-doped magnesium oxide nanocomposite compositions, metal A is titanium or zinc. In other particular embodiments, metal B is calcium or strontium.

In one particular embodiment of the co-doped magnesium oxide nanocomposite compositions, metal A is zinc and metal B is calcium.

In certain embodiments of the described compositions, the co-doped magnesium oxide nanocomposite has the formula of $(A_XB_Y)Mg_{(1-Y)-X}O$, wherein X is the atomic ratio of metal A to the magnesium oxide, and Y is the atomic ratio of metal B to the magnesium oxide. In some embodiments, X ranges from 0 to about 0.1 and Y ranges from 0 to about 0.1.

Also provided herein are antimicrobial and antineoplastic compositions which include the described co-doped magnesium oxide nanocomposite compositions of the preceding embodiments.

With the development of the antimicrobial co-doped magnesium oxide nanocomposite compositions described herein, the current disclosure also provides a method for inhibiting microbial growth and/or eliminating microbial contamination by contacting a microbe with any of the described co-doped magnesium oxide nanocomposite compositions.

In particular embodiments of the described methods, the microbe is bacteria, virus, or fungi, which can in certain embodiments be on a surface or in a subject (e.g., on a wound on the surface of subject). In other embodiments, the surface is an inanimate object or on a subject (e.g., on the skin of a subject). In still other embodiments, the co-doped magnesium oxide nanocomposite is administered directly onto a subject on or is incorporated in a wound dressing.

The foregoing and other objects, features, and advantages will become more apparent from the following detailed description, which proceeds with reference to the accompanying figures.

DETAILED DESCRIPTION

I. Terms

Figure 1:
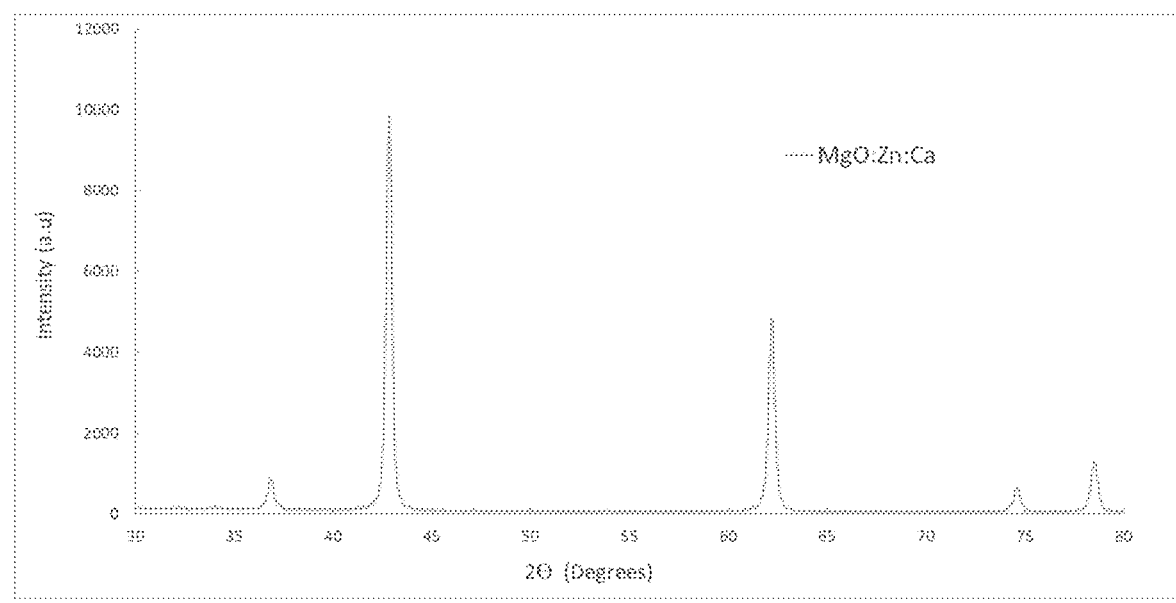
FIG. 1 shows the x-ray diffraction (XRD) pattern demonstrating a crystalline periclase structure of the Zn(II) and Ca(II) co-doped MgO produced using oxalic acid as the organic precipitant.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all molecular weight or molecular mass values are approximate, and are provided for description. Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

In case of conflict, the present specification, including explanations of terms, will control. In addition, all the materials, methods, and examples are illustrative and not intended to be limiting.

Administration: The introduction of a composition into or onto a subject by a chosen route. For example, the described co-doped magnesium oxide nanocomposite compounds can be administered locally at a wound site by any method known to the art of contacting a surface with a compound. In particular examples, the compounds are administered directly as part of a topical formulation. In other examples, the compounds are embedded onto or into a solid substrate that contacts a subject.

Antimicrobial agent: A compound that inhibits, prevents, or eradicates the growth, replication, spread or activity of a microorganism. In a particular embodiment, an antimicrobial agent is a described co-doped magnesium oxide nanocomposite. When used generally, an antimicrobial agent can inhibit, prevent, or eradicate the growth and spread of living microbes such as bacteria and fungi and/or non-living viral microbes. A microbe is inhibited when its presence or activity is decreased by at least 10%, at least 20%, at least 30%, at least 50%, at least 80%, at least 100% or at least 250% or more as compared to a microbe that has not been contacted with the compound. An agent that eradicates a microbe or prevents its growth is also known as a microbicidal agent.

Composite: A material composed of two or more constituent parts, which are generally structurally and physically distinct. A nanocomposite material is of a size in the nanometer (nm) range, typically 1 to 1000 nm.

Contacting: Placement in direct physical association; including contact of a surface by a composition both in solid and liquid forms. Contacting can occur in vivo by administering to a subject.

Doped (metal oxide): A metal oxide compound into which impurities are intentionally introduced. A co-doped composite compound contains multiple impurities. In particular embodiments of the nanocomposites described herein magnesium oxide is co-doped with zinc and calcium.

Effective amount of a compound: A quantity of compound sufficient to achieve a desired effect. In a therapeutic context, a therapeutically effective amount of a compound is that amount to achieve a desired effect in a subject being treated. For example, the therapeutically effective amount of the described nanocomposites will be the amount necessary to provide antimicrobial effects when brought into contact with a wound or when coated on an inanimate surface.

Periclase: Crystalline periclase is the rectangular crystalline structure known to be formed by MgO crystals, and is similarly shared by the co-doped MgO nanomaterial produced and described herein.

Pharmaceutically acceptable carriers: The pharmaceutically acceptable carriers useful in this disclosure are conventional. *The Science and Practice of Pharmacy,* Adeboye Adejare, Ed., 23rd Edition (2020), describes compositions and formulations suitable for pharmaceutical delivery of the compounds herein disclosed. In general, the nature of the carrier will depend on the particular mode of administration being employed, for example for use as a topical agent in an ointment, suspension, cream, or similar suspension.

Subject: Living multi-cellular organisms, including vertebrate organisms, a category that includes both human and non-human mammals.

Under conditions sufficient for [carrying out a desired activity]: A phrase that is used to describe any environment that permits the desired activity.

Wound: An injury to living tissue which can, but does not require breaking skin or bleeding. Particular non-limiting examples of wounds include bruises, burns, and cuts (of varying depths and severity). Wounds can be unintentional, such as resulting from a fall, but can also be intentional, such as a result of surgery or other medical procedure.

Wound dressing: Any covering of any material used to cover a wound. In particular embodiments, wound dressings can be of natural or synthetic fabrics. In other embodiments, wound dressings can be films composed of or including the described compositions. In particular embodiments, a wound dressing does not include any active material. In other embodiments, a wound dressing includes the described compositions, alone, or with other therapeutic agents.

II. Co-Doped Magnesium Oxide Nanocomposite Compositions

It was previously described that doped magnesium oxide nanocompositions exhibit antimicrobial effects (V. Rajendran et al, IOP Conf. Ser.: Mater. Sci. Eng. Vol. 360, 2018). The current disclosure provides newly-developed co-doped magnesium oxide nanocomposites that provide robust antimicrobial properties and are biocompatible and less toxic.

Described herein are co-doped magnesium oxide nanocomposites that maintain a crystalline periclase structure, and which are highly biocompatible, and possess antimicrobial properties (antibacterial and/or antifungal properties), antineoplastic properties (e.g., for use in methods of treating cellular proliferation diseases and conditions), or combinations thereof. The described magnesium oxide nanocomposites are co-doped with a combination of two metals, referred to herein as "metal oxide A" (or "metal A") and "metal oxide B" (or "metal B"). Metal oxide A is a transition metal and metal oxide B is an alkali or alkaline-earth metal.

In particular embodiments, metal A is a transition metal selected from titanium, manganese, iron, zirconium, or zinc. In one embodiment, metal A is a soluble metal salt wherein the metal portion is selected from zinc and titanium.

In particular embodiments, metal B is an alkali or alkaline earth metal selected from sodium, potassium, calcium, strontium, or barium. In one embodiment, metal B is selected from calcium or strontium.

In further particular embodiments, metal A is zinc. In other embodiments, metal B is calcium. In still other embodiments, the described nanocomposite is a magnesium oxide nanocomposite co-doped with zinc and calcium.

In particular embodiments, the co-doped magnesium oxide nanocomposite comprises formula $(A_XB_Y)Mg_{(1-Y)-X}O$, wherein X is the atomic ratio of a metal A to the magnesium oxide and Y is the atomic ratio of a metal B to the magnesium oxide. Generally, the value of X in the magnesium oxide nanocomposite ranges from 0 to about 0.1. In various embodiments, such as from 0 to about 0.05, from 0 to about 0.03, or from 0 to about 0.02. In one embodiment, the value of X is 0.01. In general, the value of Y in the magnesium oxide nanocomposite ranges from 0 to about 0.2, such as from 0 to about 0.07 or from about 0 to about 0.05. In another embodiment, the value of Y can be 0.002 or 0.01.

The crystalline structure of the co-doped magnesium oxide nanocomposite corresponds mainly to a typical periclase structure. The crystal structure of the magnesium oxide nanocomposites can be determined by methods known in the art. Non-limiting methods for determination of the crystal structure are Raman spectrometry, high resolution transition electron microscopy (HR-TEM/EDS), x-ray crystallography, or combinations thereof.

III. Processes for Preparing Co-Doped Magnesium Oxide Nanocomposites

Additionally disclosed herein are processes for preparing the described co-doped magnesium oxide nanocomposite. The process includes: (a) providing a first aqueous solution comprising a soluble organic salt of magnesium; a soluble organic salt of metal A as described above; and a soluble organic salt of metal B as described above; (b) providing a second aqueous solution comprising at least one soluble organic anion; (c) admixing the first aqueous solution with the second aqueous solution to form an insoluble organic magnesium nanocomposite precursor; (d) isolating the insoluble organic magnesium nanocomposite precursor; (e) drying the insoluble organic magnesium nanocomposite precursor; and (f) thermal decomposition of the insoluble organic magnesium nanocomposite precursor to form the co-doped magnesium oxide nanocomposite. The process can be conducted in batch, semi-continuous, or continuous mode.

(a) First Aqueous Solution

The process commences by preparing the first aqueous solution comprising a soluble organic magnesium salt; a soluble organic salt of metal A; a soluble organic salt of metal B.

A wide variety of anions can be used for soluble magnesium salt, the soluble metal A salt, and the soluble metal B salt. An important aspect of these anions is that the anion is readily exchangeable, soluble in aqueous solution, non-toxic, pH neutral, and thermally decomposable. Non-limiting examples of suitable anions can be citrates, acetate, propionate, any soluble organic salt, or combinations thereof. In a particular embodiment, the soluble magnesium salt, the soluble metal A salt, and the soluble metal B salt are acetates.

In other embodiments, the first aqueous solution can further comprise one or more different soluble salts in addition to the soluble magnesium salt, soluble metal A salt, and soluble metal B salt. Examples of such soluble salts include magnesium acetate, magnesium nitrate, magnesium chloride, zinc acetate, zinc nitrate, and zinc chloride.

The total concentration of soluble magnesium salt, soluble metal A salt, and soluble metal B salt in water can range from about 0.01M (moles/liter) to about 1.0M. In various embodiments, the total concentration can range from about 0.01M to about 1.0M, from about 0.03M to about 0.5M, or from about 0.05M to about 0.3M. In a particular embodiment, the total concentration of a soluble magnesium salt; a soluble metal A salt, and soluble metal B salt can be about 0.3M. In other embodiments, the amount of metal A and metal B salts can be expressed as % of the magnesium (e.g. MgO) concentration. In one embodiment the metal A and metal B salts are about 0.5% to 2.0% of the MgO concentration.

In various embodiments, the preparation of the first aqueous solution can be conducted at a temperature ranging from about 10° C. to about 40° C., such as from about 15° C. to about 35° C., from about 20° C. to about 30° C., or other temperature ranges in between. In one embodiment, the preparation of the first aqueous solution can be conducted at room temperature (~25° C.). The reaction typically is performed under ambient pressure. The reaction can also be conducted under an inert atmosphere or air, for example under nitrogen, argon, or helium.

The duration for preparing the first aqueous solution can and will vary depending on factors such as the temperature, the type of mixing equipment utilized, and the type of precursors utilized. Generally, the duration of the preparation of the first aqueous solution can range from about 5 minutes to about 12 hours. In various embodiments, the duration of the preparation of the first aqueous solution can range from about 5 minutes to about 30 minutes, from about 30 minutes to about 2 hours, from about 2 hours to about 4 hours, from about 4 hours to about 10 hours, or from about 10 hours to about 12 hours. The preparation of the first aqueous solution continues until homogeneity is achieved.

(b) Second Aqueous Solution

The second aqueous solution comprises at least one soluble anion source that is readily exchangeable, soluble in aqueous solution, non-toxic, and thermally decomposable. Non-limiting examples of suitable soluble anion sources can be bicarbonate, carbonate, oxalates, malates, oxalic acid, malic acid, or combinations thereof. In a particular embodiment, the soluble anion in the second aqueous solution is ammonium carbonate, oxalic acid, or ammonium oxalate. In a particular embodiment, the soluble anion source is carbonate, and particularly from sodium carbonate.

The concentration of at the least one soluble anion source in the second aqueous solution can range from a concentration of about 0.10M to about 1.0M. In various embodiments, the concentration of the at least one soluble anion source in the second aqueous solution can range in concentration from about 0.05M to about 3.0M, from about 0.1M to about 20M, or from about 0.15M to about 0.5M. In a particular embodiment, the concentration of the at least one soluble anion source in the second aqueous solution can be about 0.3M.

In particular embodiments, the second aqueous solution further comprises a stabilizer. Non-limiting examples of stabilizers for use in the current methods include a polyethylene glycol (PEG), polypropylene glycol (PPG), polyvinylpyrrolidone (PVP), polyvinylalcohol (PVA), polyoxyethylene, or combinations thereof. In one embodiment, the stabilizer used in the second aqueous solution is PVP.

The concentration of the stabilizer in the second aqueous solution can range from about 20 g/L to about 0.1 g/L. In various embodiments, the concentration of the stabilizer in the second aqueous solution can range from about 10 g/L to about 1 g/L. In a particular embodiment, the concentration of the stabilizer in the second aqueous solution is about 5 g/L.

The process for preparing the second aqueous solution can further include an organic solvent. The addition of the organic solvent can cause a sudden change of the dielectric constant and change the dynamic of precipitation of the magnesium oxide nanocomposite precursor. These changes can further lead to a hierarchic structure, an anisotropic configuration of the magnesium oxide nanocomposite precursor, or combinations of both of these properties. An additional property of the solvent is that solvent is volatile, enabling removal of excess amounts of solvent. Non-limiting examples of suitable solvents for use in the second aqueous solution can be methanol, ethanol, propanol, isopropanol, acetone, or combinations thereof. In a particular embodiment, the solvent used in the second aqueous solution is ethanol.

Generally, the volume percent of the solvent in the second aqueous solution can range from about 0.01 volume % to about 0.1 volume %. In various embodiments, the volume percent of the solvent in the second aqueous solution ranges from about 0.01 volume % to about 0.1 volume %, from about 0.02 volume % to about 0.08 volume %, or from about 0.03 volume % to about 0.07 volume %. In a particular embodiment, the volume percent of the solvent in the second aqueous solution is about 0.02 volume %.

The second aqueous solution is prepared by forming a reaction mixture comprising at least one soluble anion source, a stabilizer, water, and an optional solvent. These components can be added all at the same time, sequentially, or in any order, and are then blended together in any known mixing equipment or reaction vessel until the mixture achieves a clear solution.

The preparation of the second aqueous solution can be conducted at a temperature that ranges from about 10° C. to about 100° C. In various embodiments, the temperature of the preparation can range from about 30° C. to about 90° C., from about 50° C. to about 80° C., or from about 60° C. to about 75° C. In one embodiment, the temperature of the preparation can be about 70° C. The preparation typically is performed under ambient pressure. The preparation can also be conducted under air or an inert atmosphere, for example under nitrogen, argon, or helium.

The duration for preparing the second aqueous solution and will vary depending on many factors, such as the temperature, the method of mixing, and amount of the at least one anion source being mixed. The duration of the reaction can range from about 5 minutes to about 12 hours. In some embodiments, the duration of the reaction can range from about 5 minutes to about 30 minutes, from about 30 minutes to about 2 hours, from about 2 hours to about 4 hours, from about 4 hours to about 10 hours, or from about 10 hours to about 12 hours.

(c) Preparation of the Insoluble Co-Doped Magnesium Oxide Nanocomposite Precursor To prepare the insoluble co-doped magnesium oxide nanocomposite precursor, the first aqueous solution is contacted with the second aqueous solution. Once the second aqueous solution is contacted with the first aqueous solution, a chemical reaction occurs according to the following scheme:

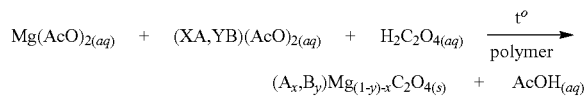

In a particular embodiment, the second aqueous solution includes oxalic acid or ammonium salt. An advantage of using oxalic acid or ammonium salt in the second aqueous solution is that the by-product, acetic acid or ammonium acetate, is water soluble, and is easily removed from the insoluble magnesium oxide nanocomposite precursor. The trace amount of ammonium acetate or acetic acid they remain following this reaction is readily thermally decomposed in the process. In another particular embodiment, the second aqueous solution includes a carbonate salt, for example sodium carbonate.

The insoluble magnesium oxide nanocomposite precursor can be prepared by forming a reaction mixture comprising the first aqueous solution, the second aqueous solution, and the optional solvent. The insoluble magnesium oxide nanocomposite precursor is produced by blending the above components in any known mixing equipment or reaction vessel or static mixer until the mixture achieves completeness of reaction.

Generally, the first aqueous solution is added to the second aqueous solution immediately in a batch or by a static mixer continuously in a range from about 20 volume % to about 45 volume % to the first aqueous solution. The remaining portion can be added in parts after the first addition.

The speed of mixing the first aqueous solution with the second aqueous solution is critical to ensure the reaction goes to completion. In general, the speed of mixing can range from about 1 L/min to about 10 L/min. In various embodiments, the speed of mixing can range from 1 L/min to about 10 L/min, from about 2 L/min to about 8 L/min, or from about 4 L/min to about 6 L/min. In one embodiment, the speed of mixing can range from about 5 L/min to about 6 L/min.

The duration for preparing the insoluble magnesium oxide nanocomposite precursor can and will vary depending on many factors, such as the temperature and scale of the process. The duration of the reaction can range from about 5 minutes to about 6 hours. In some embodiments, the duration of the reaction can range from about 5 minutes to about 6 hours, from about 15 minutes to about 4 hours, or from about 20 minutes to about 1 hour. In one embodiment, the duration for preparing the insoluble magnesium oxide nanocomposite precursor can be about 30 minutes.

(d) Isolating the Insoluble Co-Doped Magnesium Oxide Nanocomposite Precursor

The next step in the process is isolating the insoluble magnesium oxide nanocomposite precursor from the reaction mixture in step (c). It will be appreciated that there are many methods of isolating the insoluble magnesium oxide nanocomposite precursor from the reaction mixture in step (c). Non-limiting methods are filtration, centrifugal separation, decantation, or combinations thereof. After isolation, the insoluble magnesium oxide nanocomposite precursor is rinsed with water, ethanol, or combinations thereof until the supernatant is colorless or the precursor color remains constant.

(e) Drying the Insoluble Co-Doped Magnesium Oxide Nanocomposite Precursor.

The next step in the process is drying the insoluble magnesium oxide nanocomposite precursor from the reaction mixture in step (d) to remove excess solvent from the insoluble magnesium oxide nanocomposite precursor. As appreciated by the skilled artisan, many devices are available to dry the precursor. Non-limiting examples for drying the solid are batch driers, convection ovens, rotary dryers, drum dryers, kiln dryers, flash dryers, or tunnel dryers.

In general, the drying of the insoluble metal oxide nanocomposite precursor can be conducted at a temperature that ranges from about 30° C. to about 120° C. In various embodiments, the temperature of the preparation can range from about 30° C. to about 120° C., from about 40° C. to about 100° C., or from about 50° C. to about 80° C. In one embodiment, the temperature of drying is about 60° C. The preparation typically is performed under ambient pressure. The preparation can also be conducted under air or an inert atmosphere, for example under nitrogen, argon, or helium.

The duration for drying the insoluble magnesium oxide nanocomposite precursor and will vary depending on many factors, such as the temperature, the amount of the precursor, and type of the dryer. The duration of the reaction can range from about 30 minutes to about 48 hours. In some embodiments, the duration of the reaction can range from about 30 minutes to about 48 hours, from about 1 hour to about 24 hours, or from about 2 hours to about 4 hours. In one embodiment, the duration for drying the insoluble metal oxide semiconductor precursor can be about 3 hours, or until the drying the insoluble magnesium oxide nanocomposite precursor reaches less than 10% moisture.

(f) Thermal Decomposition of the Insoluble Co-Doped Magnesium Oxide Nanocomposite Precursor Forming the Co-Doped Magnesium Oxide Nanocomposite The next step in the process is thermal decomposition of the insoluble magnesium oxide nanocomposite precursor forming the magnesium oxide nanocomposite. This step removes the thermally labile ligand forming the oxides, removes by-products, and removes impurities that were not removed in step (d). As appreciated by the skilled artisan, carbon, hydrogen, and excessive oxygen are released as carbon dioxide and water vapor from the thermally labile ligands, by-products, and impurities. In one embodiment, the insoluble co-doped magnesium oxide nanocomposite precursor comprising a magnesium, zinc, strontium, and/or calcium is thermally decomposed to form the co-doped magnesium oxide nanocomposite. This reaction can be depicted according to the following scheme:

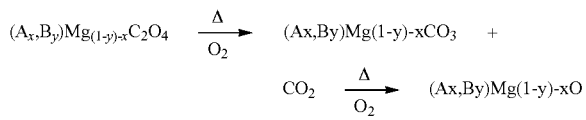

In general, thermal decomposition of the insoluble magnesium oxide nanocomposite precursor is conducted at a temperature that ranges from about 300° C. to about 1200° C. In various embodiments, the temperature of the preparation can range from about 400° C. to about 1100° C., from about 500° C. to about 1000° C., or from about 550° C. to about 950° C. In one embodiment, the temperature of annealing can be about 950° C. The preparation typically is performed under ambient pressure. The preparation can also be conducted under air or an inert atmosphere, for example under nitrogen, argon or helium.

The duration for thermal decomposition of the insoluble co-doped magnesium oxide nanocomposite precursor will vary depending on many factors, such as the temperature, the amount of the precursor, and type of the dryer (e.g. furnace or oven). The duration of the reaction can range from about 5 minutes to about 48 hours. In some embodiments, the duration of the reaction can range from about 10 minutes to about 48 hours, from about 15 hours to about 24 hours, or from about 2 hours to about 4 hours. In a one embodiment, the duration for annealing the insoluble metal salt co-doped magnesium oxide nanocomposite precursor is about 2 hours.

IV. Uses of the Co-doped Magnesium Oxide Nanocomposite Composition

The co-doped magnesium oxide nanocomposites disclosed herein can be used in a wide variety of medical and industrial applications.

In particular embodiments, the described nanocomposites can be used in antimicrobial compositions for coating articles and/or incorporated into materials and objects such as but not limited to fabrics, bandages, textiles, catheters, electrospun fibers, and syringe needles. In other embodiments, the described nanocomposites can be used in topical formulations for human and animal use to inhibit or prevent microbial growth in a wound.

In other embodiments, the described co-doped magnesium oxide nanocomposites can be used as components of photovoltaic cells comprising the magnesium oxide nanocomposite. In other embodiments, the described nanocomposites can be incorporated into paints, plastics, or coatings.

In one embodiment, the method comprises coating or incorporation into an article such as but not limited to fabric bandages, textiles, catheters, electrospun fibers, and needles, with an effective amount of the co-doped magnesium oxide nanocomposite. The method comprises dispersing the magnesium oxide nanocomposite in a solvent suitable for use with the intended material (such as ethanol, water, silicone, or combinations thereof), applying the dispersed magnesium oxide nanocomposite onto the article, thereby forming at least one layer of the magnesium oxide nanocomposite on the article, and drying the layer to remove the solvent using heat, vacuum, or an inert gas. When coated with the described nanocomposite, the article can be used in applications requiring or benefiting from an antimicrobial effect, such as an antibacterial effect, antifungal effect, or combinations thereof. The dispersed magnesium oxide nanocomposite can be applied to the article by painting, spraying, or dipping, or any other method known to the art for applying a dispersed material to an article.

In another embodiment, the described co-doped magnesium oxide nanocomposites can be used in antimicrobial compositions of significantly reduced toxicity for treatment of acute or chronic wounds. Such methods include mixing the co-doped magnesium oxide nanocomposite into a topical formulation and then applying the topical formulation to a surface on the subject. In particular embodiments, the formulation is applied to an infected area. In other embodiments, the formulation is applied to an area that is susceptible to infection, such as an open wound or severe burn. The described topical formulation provides antimicrobial properties including antibacterial and/or antifungal properties to the subject and inhibits or eliminates the microbe, such as bacterium, and/or the fungus. Various topical formulations can be used to provide the co-doped magnesium oxide nanocomposite. Topical formulations for use in the current methods include conventional nontoxic pharmaceutically acceptable carriers, adjuvants, and vehicles as appropriate. In other particular embodiments, topical administration of the described nanocomposites is achieved by a transdermal administration route such as transdermal patches or iontophoresis devices.

In still another embodiment, the described co-doped magnesium oxide nanocomposite can be added to a hydrophobic and/or anhydrous coating for coating the surface of inanimate objects. Such methods include mixing the co-doped magnesium oxide nanocomposite with a hydrophobic coating, thereby creating an antimicrobial, such as antibacterial and/or antifungal, surface on the coated article. Non-limiting examples of articles that can be coated with the described compositions include metals, glass, plastic, and ceramics used in many applications like food packaging or sutures.

In another embodiment, the magnesium oxide nanocomposite is mixed or dispersed in a paint, plastics, or various coatings. The resulting paints, plastics, or various coatings would provide antimicrobial properties, such as antibacterial and/or antifungal properties to the paint, plastics, or various coatings.

As noted, the described magnesium oxide nanocomposites can be used in various applications to inhibit and/or prevent microbial growth on an animate or inanimate surface. Examples of microbes that can be targeted include bacteria (Gram positive and Gram negative) and fungi. Particular examples of bacteria that can be inhibited by use of the described compounds include, but are not limited to, species of *Staphylococcus*, such as *Staphylococcus aureus*, *Staphylococcus epidermidis*, and the like; *Enterococcus*, such as *Enterococcus faecalis*, *Enterococcus faecium*, and the like; *Salmonella*, such as *Salmonella typhi*, *Salmonella typhimurium*, *Salmonella enterica*, and the like; *Escherichia*, such as *Escherichia coli*, and the like; of *Streptococcus*, such as *Streptococcus pneumoniae*, *Streptococcus pyogenes*, *Streptococcus agalactiae*, and the like; *Helicobacter*, such as *Helicobacter pylori*, and the like; *Campylobacter*, such as *Campylobacter jejuni*, and the like; as well as the species of genera, *Yersinia, Chlamydia, Coxilla, Ehrlichia, Francisella, Legionella, Pasteurella, Brucella, Proteus, Klebsiella, Enterobacter, Tropheryma, Acinetobacter, Aeromonas, Alcaligenes, Capnocytophaga, Bacillus, Clostridium, Corynebacterium, Erysipelothrix, Listeria, Pseudomonas*, and the like. Examples of microbes inhibited by the described compounds also include infections caused by fungi, such as *Candida albicans, Microsporum canis, Sporothrix schenckii, Trichophyton rubrum, Trichophyton mentagrophytes, Malassezia furfur, Pityriasis versicolor, Exophiala werneckii, Trichosporon beigelii, Coccidioides immitis, Blastomyces dermatitidis, Aspergillus fumigatus, Epidermophyton* spp., *Fusarium* spp., *Zygomyces* spp., *Rhizopus* spp. *Mucor* spp., and so forth.

Furthermore, the described compounds can be applied for inhibiting or preventing the growth of microorganisms that are resistant to at least one antimicrobial agent. The term "antimicrobial agent" used herein refers to any naturally or synthetically derived agent that kills microorganisms or inhibits the growth thereof, directly or indirectly, and includes conventional antibiotics as well as synthetic chemotherapeutic agents, such as sulfonamides, isoniazid, ethambutol, AZT, synthetic peptide antibiotics, and the like. Thus, in a specific embodiment, the microbes inhibited or prevented by the described compounds include antimicrobial-resistant strains of microorganisms mentioned above, in particular, of *Staphylococcus aureus, Enterococcus faecium, Enterococcus faecalis, E. coli, Salmonella typhi, Campylobacter jejuni, Klebsiella pneumoniae, Neisseria gonorrhoeae, Candida albicans*, and the like. More specifically, such antimicrobial-resistant organisms include methicillin-resistant *Staphylococcus aureus* (MRSA), vancomycin-resistant enterococci (VRE), ampicillin-resistant *E. coli* (e.g., *E. coli* O157:H7), fluoroquinolone-resistant *Salmonella thyphi*, ceftazidime-resistant *Klebsiella pneumoniae*, fluoroquinolone-resistant *Neisseria gonorrhoeae*, and the like.

The described nanocomposites are biocompatible in comparison to other doped and co-doped metal and heavy metal nanoparticle compounds. Such properties enable use on human and animal subjects and devices that contact such subjects, as well as lessen the environmental impact of such compounds when used in industrial applications.

Moreover, as described herein, particular embodiments of the co-doped nanocomposites unexpectedly demonstrate increased antimicrobial properties in comparison to other co-doped nanocomposites. It will be appreciated that among the benefits of such compounds with increased activity is the ability to provide a robust antimicrobial efficacy while needing comparatively less amount of compound to achieve the effect.

In a further embodiment, the described nanocomposite compounds can be used in industrial applications. Particular examples of such applications include environmental clean-up and purification activities, including degradation of organic contaminants and dyes in the air and water purification. It will be appreciated that for such embodiments, the described nanocomposites are provided by any method known to the art of contacting a material to be purified or from which toxins are to be degraded or removed. Particular examples include filters and filtration systems for air and water into and/or onto which the described nanocomposites are embedded or sprayed.

The following examples are provided to illustrate certain particular features and/or embodiments. These examples should not be construed to limit the disclosure to the particular features or embodiments described.

EXAMPLES

Example 1: Preparation of the $(A_X, B_Y)Mg_{(1-Y)-X}O$ Nanocomposite when X and Y are 0

Into a 5 L reactor was added 965 g $Mg(OAc)_2$ tetrahydrate and 3 L deionized (DI) water at room temperature. This mixture was stirred until the solids dissolved (first solution). Into a separate 20 L reactor equipped with mechanical stirring was 12 L deionized water (DI). To this solution was added 567.3 g $H_2C_2O_4$ dihydrate. This mixture was stirred until the solids dissolved at room temperature (second solution). Once the second solution becomes homogeneous, the first solution was immediately added into the 20 L reactor maintaining the mechanical stirring at 200 rpm. After the addition of the solution is complete, the reaction was stirred for an additional 30 minutes where a solid precipitate formed. The stirring was stopped, and the solid precipitate was filtered using vacuum filtration. The solids were washed several times with DI water. After the filter cake was dried. The solids were removed and dried in a vacuum oven at 40° C. for 3 hours.

The solids were removed from the vacuum oven and cooled to room temperature. The solids were transferred to a porcelain crucible and introduced into an annealing furnace at atmospheric pressure and the solid was heated at 950° C. for 2 hours, yielding 180 g of nanomaterial.

Example 2: Preparation of the $(A_X, B_Y)Mg_{(1-Y)-X}O$ Nanocomposite when X ($Zn^{+2}$) is 0.01 and Y is 0

Into a 5 L reactor was added 955.4 g $Mg(OAc)_2$ tetrahydrate and 10 g of $Zn(AcO)_2$ dihydrate in 3 L deionized (DI) water at room temperature. This mixture was stirred until the solids dissolved (first solution). Into a separate 20 L reactor equipped with mechanical stirring was 12 L deionized water (DI). To this solution was added 567.3 g $H_2C_2O_4$ dihydrate. This mixture was stirred until the solids dissolved at room temperature (second solution). Once the second solution becomes homogeneous, the first solution was immediately added into the 20 L reactor maintaining the mechanical stirring at 200 rpm. After the addition of the solution is complete, the reaction was stirred for an additional 30 minutes where solids began to precipitate. The precipitated solids were filtered using vacuum filtration. The solids were washed several times with DI water and then filtered. After the filter cake was dried, the solids were washed with additional DI water. The solids were removed and dried in a vacuum oven at 40° C. for 3 hours.

The solids were removed from the vacuum oven and cooled to room temperature. The solids were then transferred to a porcelain crucible. The solids were transferred to a porcelain crucible and introduced into an annealing furnace at atmospheric pressure and the solid was heated at 950° C. for 2 hours, yielding 182 g of nanomaterial.

Example 3: Preparation of the $(A_X,B_Y)Mg_{(1-Y)-X}O$ Nanocomposite when X is 0 and Y ($Ca^{+2}$) is 0.01

Into a 5 L reactor was added 955.4 g $Mg(OAc)_2$ tetrahydrate and 8 g $Ca(AcO)_2$ monohydrate in 3 L deionized (DI) water at room temperature. This mixture was stirred until the solids dissolved (first solution). Into a separate 20 L reactor equipped with mechanical stirring was 12 L deionized water (DI). To this solution was added 567.3 g $H_2C_2O_4$ dihydrate. This mixture was stirred until the solids dissolved at room temperature (second solution). Once the second solution becomes homogeneous, the first solution was immediately added into the 20 L reactor maintaining the mechanical stirring at 200 rpm. After the addition of the solution was complete, the reaction was stirred for an additional 30 minutes where solids started to precipitate. The precipitated solids were filtered using vacuum filtration. The solids were washed several times with DI water and then filtered. After the filter cake was dried, the solids were washed with additional DI water. The solids were removed and dried in a vacuum oven at 40° C. for 3 hours.

The solids were removed from the vacuum oven and cooled to room temperature. The solids were transferred to a porcelain crucible. The solids were transferred to a porcelain crucible and introduced into an annealing furnace at atmospheric pressure and the solid was heated at 950° C. for 2 hours, yielding 182 g of nanomaterial.

Example 4: Preparation of the $(A_X,B_Y)Mg_{(1-Y)-X}O$ Nanocomposite when X ($Zn^{+2}$) is 0.01 and Y ($Ca^{+2}$) is 0.01

Into a 5 L reactor was added 946 g $Mg(OAc)_2$ tetrahydrate, 7.85 g $Ca(AcO)_2$ monohydrate and 10 g $Zn(AcO)_2$ dihydrate in 3 L deionized (DI) water at room temperature. This mixture was stirred until the solids dissolved (first solution). Into a separate 20 L reactor equipped with mechanical stirring was 12 L deionized water (DI). To this solution was added 567.3 g $H_2C_2O_4$ dihydrate. This mixture was stirred until the solids dissolved at room temperature (second solution). Once the second solution becomes homogeneous, the first solution was immediately added into the 20 L reactor maintaining the mechanical stirring at 200 rpm. After the addition of the solution was complete, the reaction was stirred for an additional 30 minutes where solids started to precipitate. The precipitated solids were filtered using vacuum filtration. The solids were washed several times with DI water and then filtered. After the filter cake was dried, the solids were washed with additional DI water. The solids were removed and dried in a vacuum oven at 40° C. for 3 hours.

The solids were removed from the vacuum oven and cooled to room temperature. The solids were transferred to a porcelain crucible. The solids were transferred to a porcelain crucible and introduced into an annealing furnace at atmospheric pressure and the solid was heated at 950° C. for 2 hours, yielding 97 g of nanomaterial.

Elemental analysis by inductively coupled plasma atomic emission spectroscopy (ICP-AES) was carried out on nanocomposites from Examples 1-4 (following methods similar to those available online at chem.libretexts.org/Bookshelves/Analytical_Chemistry/Book%3A_Physical_Methods_in _Chemistry_and_ Nano_Science_(Barron)/01%3A_Elemental_Analysis/ 1.05%3A_ICP-AES _Analysis_of_Nanoparticles. The results are shown in Table 1:

| Sample | Mg (% w/w) | Zn (% w/w) | Ca (% w/w) |
|---|---|---|---|
| MgO | 58.8 | 0.0 | 0.0 |
| MgO:Zn | 58.3 | 1.8 | 0.0 |
| MgO:Ca | 56.7 | 0.0 | 1.0 |
| MgO:Zn:Ca | 55.6 | 1.4 | 0.9 |

Figure 2:
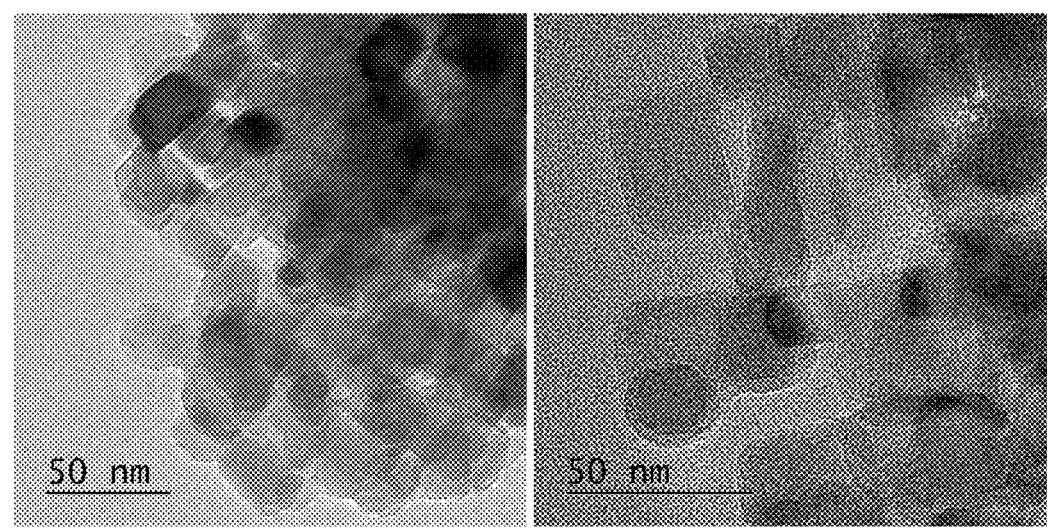
FIG. 2 shows high resolution transmission electron microscopy (HRTEM) image analysis to confirm the morphology of Zn(II) and Ca(II) co-doped MgO produced using oxalic acid as the organic precipitant.

The physical structure of the co-doped MgO:Zn:Ca nanocomposite was further assayed and verified to be periclase by x-ray diffraction (FIG. 1) and high-resolution transmission electron microscopy (HRTEM) (FIG. 2).

Example 5: Preparation of the $(A_X,B_Y)Mg_{(1-Y)-X}O$ Nanocomposite when X ($Zn^{+2}$) is 0.01 and Y ($Sr^{+2}$) is 0.01

Into a 5 L reactor was added 946 g $Mg(OAc)_2$ tetrahydrate, 9.6 g $Sr(AcO)_2$ monohydrate and 10 g $Zn(AcO)_2$ dihydrate in 3 L deionized (DI) water at room temperature. This mixture was stirred until the solids dissolved (first solution). Into a separate 20 L reactor equipped with mechanical stirring was 12 L deionized water (DI). To this solution was added 567.3 g $H_2C_2O_4$ dihydrate. This mixture was stirred until the solids dissolved at room temperature (second solution). Once the second solution becomes homogeneous, the first solution was immediately added into the 20 L reactor maintaining the mechanical stirring at 200 rpm. After the addition of the solution was complete, the reaction was stirred for an additional 30 minutes where solids started to precipitate. The precipitated solids were filtered using vacuum filtration. The solids were washed several times with DI water and then filtered. After the filter cake was dried, the solids were washed with additional DI water. The solids were removed and dried in a vacuum oven at 40° C. for 3 hours.

The solids were removed from the vacuum oven and cooled to room temperature. The solids were transferred to a porcelain crucible. The solids were transferred to a porcelain crucible and introduced into an annealing furnace at atmospheric pressure and the solid was heated at 950° C. for 2 hours, yielding 185 g of nanomaterial.

Example 6: Preparation of the $(A_X,B_Y)Mg_{(1-Y)-X}O$ Nanocomposite when X ($Ti^{+4}$) is 0.01 and Y ($Ca^{+2}$) is 0.01

Into a 5 L reactor was added 946 g $Mg(OAc)_2$ tetrahydrate, 7.85 g $Ca(AcO)_2$ monohydrate and 13.2 g $(NH_4)_2TiO(C_2O_4)_2$ monohydrate in 3 L deionized (DI) water at room temperature. This mixture was stirred until the solids dissolved (first solution). Into a separate 20 L reactor equipped with mechanical stirring was 12 L deionized water (DI). To this solution was added 567.3 g $H_2C_2O_4$ dihydrate. This mixture was stirred until the solids dissolved at room temperature (second solution). Once the second solution becomes homogeneous, the first solution was immediately added into the 20 L reactor maintaining the mechanical stirring at 200 rpm. After the addition of the solution was complete, the reaction was stirred for an additional 30 minutes where solids started to precipitate. The precipitated solids were filtered using vacuum filtration. The solids were washed several times with DI water and then filtered. After the filter cake was dried, the solids were washed with additional DI water. The solids were removed and dried in a vacuum oven at 40° C. for 3 hours.

The solids were removed from the vacuum oven and cooled to room temperature. The solids were transferred to a porcelain crucible. The solids were transferred to a porcelain crucible and introduced into an annealing furnace at atmospheric pressure and the solid was heated at 950° C. for 2 hours, yielding 187 g of nanomaterial.

Example 7: Preparation of the $(A_X,B_Y)Mg_{(1-Y)-X}O$ Nanocomposite when X ($Zn^{+2}$) is 0.01 and Y ($Ca^{+2}$) is 0.01 Using Ammonium Oxalate for Second Solution Into a 5 L reactor was added 946 g $Mg(OAc)_2$ tetrahydrate, 7.85 g $Ca(AcO)_2$ monohydrate and 10 g $Zn(AcO)_2$ dihydrate in 3 L deionized (DI) water at room temperature. This mixture was stirred until the solids dissolved (first solution). Into a separate 20 L reactor equipped with mechanical stirring was 12 L deionized water (DI). To this solution was added 639.5 g ammonium oxalate monohydrate. This mixture was stirred until the solids dissolved at room temperature (second solution). Once the second solution becomes homogeneous, the first solution was immediately added into the 20 L reactor maintaining the mechanical stirring at 200 rpm. After the addition of the solution was complete, the reaction was stirred for an additional 30 minutes where solids started to precipitate. The precipitated solids were filtered using vacuum filtration. The solids were washed several times with DI water and then filtered. After the filter cake was dried, the solids were washed with additional DI water. The solids were removed and dried in a vacuum oven at 40° C. for 3 hours.

The solids were removed from the vacuum oven and cooled to room temperature. The solids were transferred to a porcelain crucible. The solids were transferred to a porcelain crucible and introduced into an annealing furnace at atmospheric pressure and the solid was heated at 950° C. for 2 hours, yielding 180 g of nanomaterial.

Example 8: Preparation of the $(A_X,B_Y)Mg_{(1-Y)-X}O$ Nanocomposite when X ($Zn^{+2}$) is 0.01 and Y ($Ca^{+2}$) is 0.01 Using Ammonium Carbonate for Second Solution Into a 5 L reactor was added 946 g $Mg(OAc)_2$ tetrahydrate, 7.85 g $Ca(AcO)_2$ monohydrate and 10 g $Zn(AcO)_2$ dihydrate in 3 L deionized (DI) water at room temperature. This mixture was stirred until the solids dissolved (first solution). Into a separate 20 L reactor equipped with mechanical stirring was 12 L deionized water (DI). To this solution was added 432.5 g ammonium carbonate. This mixture was stirred until the solids dissolved at room temperature (second solution). Once the second solution becomes homogeneous, the first solution was immediately added into the 20 L reactor maintaining the mechanical stirring at 200 rpm. After the addition of the solution was complete, the reaction was stirred for an additional 30 minutes where solids started to precipitate. The precipitated solids were filtered using vacuum filtration. The solids were washed several times with DI water and then filtered. After the filter cake was dried, the solids were washed with additional DI water. The solids were removed and dried in a vacuum oven at 40° C. for 3 hours.

The solids were removed from the vacuum oven and cooled to room temperature. The solids were transferred to a porcelain crucible. The solids were transferred to a porcelain crucible and introduced into an annealing furnace at atmospheric pressure and the solid was heated at 950° C. for 2 hours, yielding 97 g of nanomaterial.

Example 9: Bactericidal Effect of Co-Doped Magnesium Oxide Nanocomposites

This example compares the bactericidal effects of the co-doped magnesium oxide nanocomposites disclosed herein.

Co-doped magnesium oxide nanocomposites were prepared as described in the preceding examples, and suspended in saline to a 100 ppm concentration.

The antibacterial activity of co-doped magnesium oxide was tested against *E. coli* (ATCC 8739). To test free particles, over-night bacterial cultures in Tryptic Soy Broth (HiLabs, Israel) were harvested and washed in saline (0.86% NaCl, Bio-Lab, Israel). The bacterial concentration in suspension was estimated using a nephelometer (PhoenixSpec, BD). The suspension was then diluted accordingly to ~$10^6$ cfu/mL. Nanoparticle suspension of 200 ppm was prepared by weighing 20 mg in a 200 mL glass beaker, adding 100 mL sterilized deionized water and suspending using a sonotrode (Hielscher, Germany) for 2 min at 80% amplitude. In a 50 mL polypropylene test tube, 1 mL concentrated sodium chloride solution (7.74 g/L) was added to 8 mL of the nanoparticle suspension in water, reaching a salt concentration of 0.86 g/L as in saline. To this, 1 mL of bacterial suspension in saline ($10^6$ cfu/mL) was added to reach a bacterial concentration of $10^5$ cfu/mL. 1 mL sample was taken for enumeration of bacterial concentration at T0. The test tube was incubated shaking at 36° C., 220 rpm. After 1 h, 1 mL of sample was taken from the tube and used for preparation of serial dilutions. 1 mL solution from each dilution and without dilution was then plated in triplicates using the pour-plate method with molten Tryptic Soy Agar (HiLabs, Israel) at 45-47° C. Plates were incubated at 36° C. for 24 h-48 h, depending on the species tested. at the end of incubation, bacterial colonies were counted. Reduction in bacterial viability was determined by $\log_{10}(N_t/N_i)$, where $N_i$ and $N_t$ are the initial ($N_i$) and final ($N_t$) counts of bacteria in cfu/mL. Summary results of the anti-bacterial assays are shown in below

TABLE 2

Bactericidal effect of co-doped magnesium oxide nanocomposites. Bactericidal effect is shown as log reduction in growth.

| Example | Composition | Bactericidal activity (log reduction in growth) |
|---|---|---|
| 4 | MgO:Ca:Zn | 4.8 |
| 5 | MgO:Sr:Zn | 1.7 |
| 7 | MgO:Ca:Zn | 4.3 |
| 8 | MgO:Ca:Zn | 1.9 |

As shown in Table 2, all of the tested nanocomposites are bactericidal, though with some variation depending on the nanocomposite synthesis conditions.

Example 10: Preparation of the $(A_X,B_Y)Mg_{(1-Y)-X}O$ Nanocomposite when X ($Zn^{+2}$) is 0.01 and Y ($Ca^{+2}$) is 0.02

In a reactor, 62.4 g Magnesium Acetate tetrahydrate, 0.66 g of Zinc Acetate dihydrate, and 1.06 g of calcium acetate monohydrate were added to 0.2 L of DIW and stirred until complete dissolution (First solution). In a separate reactor, 31.76 g of Sodium Carbonate was dissolved in 0.8 L of DIW (Second solution). Once the second solution was homogeneous, the first solution was immediately added into it while maintaining the stirring. Immediate precipitation occurred, stirring was continued for another 60 minutes at room temperature. The precipitated solids were filtered using vacuum filtration. The solids were washed several times with DI water and then filtered. After the filter cake was dried, the solids were washed with additional DI water. The solids were removed and dried in a vacuum oven at 40° C. overnight. The mass of the obtained precipitate was 30 g.

The solids were removed from the vacuum oven and cooled to room temperature. The solids were transferred to a porcelain crucible, and introduced into an annealing furnace at atmospheric pressure, and the solid was heated at 950° C. for 2 hours, yielding 9.4 g of nanomaterial.

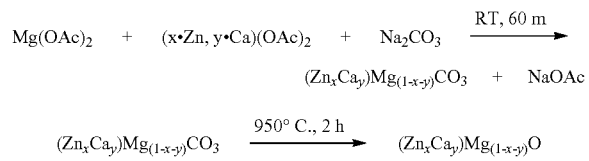

Where x = 0.01, y = 0.02

Elemental analysis of the nanocomposite was performed using inductively coupled plasma atomic emission spectroscopy (ICP-AES). The results are shown in Table 3.

TABLE 3

ICP analysis for Zn(II) and Ca(II) co-doped MgO produced using $Na_2CO_3$ as the organic precipitant.

| Sample | Mg(% w/w) | Zn(% w/w) | Ca(% w/w) |
|---|---|---|---|
| MgO:Zn:Ca | 54.47 | 1.87 | 1.26 |

Figure 3:
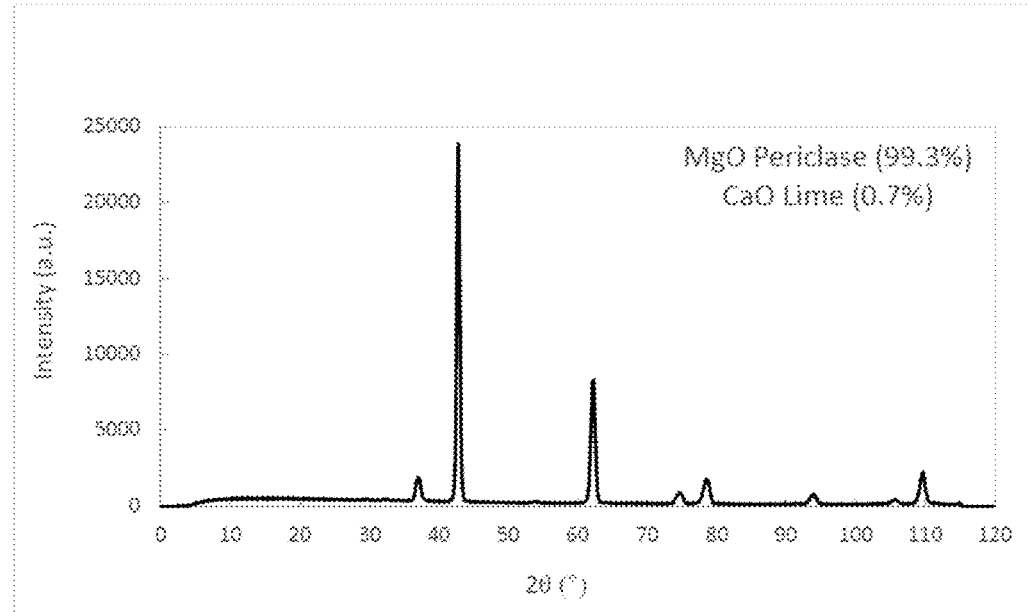
FIG. 3 shows the X-ray diffraction (XRD) pattern for crystalline periclase structure of Zn(II) and Ca(II) co-doped MgO produced using $Na_2CO_3$ as the organic precipitant.
Figure 4:
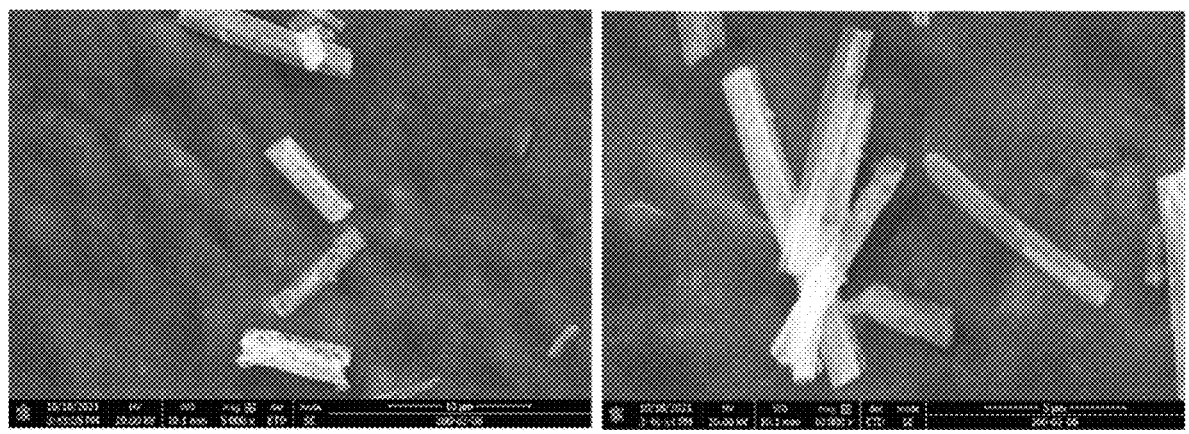
FIG. 4 is a SEM image analysis to confirm the morphology of Zn(II) and Ca(II) co-doped MgO produced using $Na_2CO_3$ as the precipitant.
Figure 5:
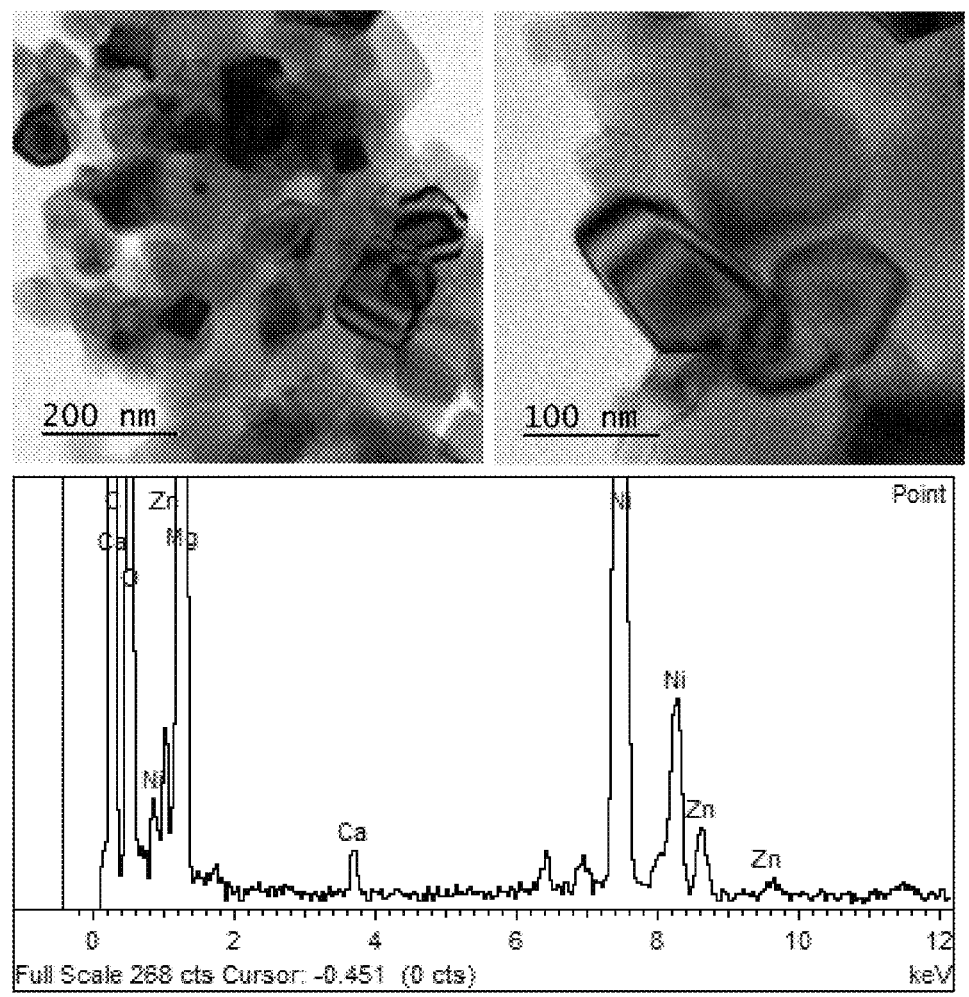
FIG. 5 (Top) shows a HRTEM image analysis to confirm the size and morphology of Zn(II) and Ca(II) co-doped MgO produced using $Na_2CO_3$ as the precipitant. (Bottom) Energy-dispersive spectroscopy (EDS) point analysis to confirm the doping composition of Zn(II) and Ca(II) co-doped MgO produced using $Na_2CO_3$ as the precipitant.

The structure and the morphology of the Zn(II) and Ca(II) co-doped MgO nanocomposite was further assayed and verified by x-ray diffraction (FIG. 3), scanning electron microscopy (SEM) (FIG. 4), and high-resolution transmission electron microscopy (HRTEM) (FIG. 5). The nanocomposite produced here was consistent with in elemental composition and in crystalline periclase structure that was produced and described in the preceding examples.

Bactericidal activity of the nanocoposite was tested against a broad-spectrum of Gram positive and Gram negative bacteria as described above. The results are shown in Table 4, and inidcate strong bactericidal activity against Gram positive and Gram negative bacteria, including antibiotic-resistant strains.

TABLE 4

Bactericidal activity of Zn(II) and Ca(II) co-doped MgO produced using $Na_2CO_3$ as the precipitant.

| | Bacterial species | Average log reduction |
|---|---|---|
| Gram negative | Escherichia coli | 5.29 |
| | Salmonella enterica serovar Typhimurium | 3.64 |
| | Klebsiella pneumoniae | 5.13 |
| Gram positive | Methicillin-resistant Staphylococcus aureus | 1.47 |
| | Listeria monocytogenes | 3.44 |
| | Enterococcus faecalis | 0.62 |
| | Staphylococcus epidermidis | 3.59 |

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A co-doped magnesium oxide nanocomposite composition comprising magnesium oxide doped with metal A and B, wherein
    metal A is a transition metal selected from the group consisting of titanium, vanadium, manganese, iron, zirconium, niobium, silver, and zinc, and
    metal B is an alkali or alkaline earth metal selected from the group consisting of lithium, sodium, potassium, calcium, strontium, and barium,
    wherein the co-doped magnesium oxide nanocomposite has the formula of $(A_XB_Y)Mg_{(1-Y)-X}O$,
    wherein X is the atomic ratio of metal A to the magnesium oxide and ranges from greater than 0 to about 0.1, and Y is the atomic ratio of metal B to the magnesium oxide and ranges from greater than 0 to about 0.1,
    and wherein the co-doped magnesium oxide nanocomposite comprises a crystalline periclase structure.

2. The composition of claim 1, wherein metal A is titanium or zinc.

3. The composition of claim 1, wherein metal B is calcium or strontium.

4. The composition of claim 1, wherein metal A is zinc and metal B is calcium.

5. An antimicrobial or antineoplastic composition comprising the co-doped magnesium oxide nanocomposite composition of claim 1.

6. A method for eliminating microbial contamination comprising, contacting a source of microbial growth or contamination with the co-doped magnesium oxide nanocomposite composition of claim 1.

7. The method of claim 6, wherein the microbial growth or contamination is of a microbe that is a bacteria, virus, or fungi.

8. The method of claim 6, wherein the microbial growth or contamination is on a surface or in a subject, and wherein the contacting is contacting the surface with the composition, or administering the composition to the subject.

9. The method of claim 8, wherein the surface is an inanimate object or on a subject.

10. The method of claim 9, wherein the co-doped magnesium oxide nanocomposite is incorporated in or on a wound dressing.

11. The method of claim 6, wherein the composition is incorporated in or coated on a fabric bandage, textile, catheter, needle, or electrospun fibers.

12. The method of claim 7, wherein the microbe is resistant to at least one anti-microbial agent.

13. The method of claim 7, wherein the bacteria is a Gram positive or Gram negative bacteria.

14. The method of claim 6, wherein the composition is incorporated into paints, plastics, or coatings.

15. The method of claim 14, wherein the coating is a hydrophobic and/or anhydrous coating.

16. The method of claim 15, wherein the coating is applied to metal, glass, plastic, or ceramics.

17. A method for treatment of a chronic or acute wound, comprising administering to a subject in need thereof a topical pharmaceutical composition comprising an effective amount of the composition of claim 1, and at least one pharmaceutically acceptable topical carrier, adjuvant, and vehicle.

18. The method of claim 17, wherein the chronic or acute wound is a burn or cut.

\* \* \* \* \*